United States Patent [19]

Goldmann et al.

[11] Patent Number: 4,642,310
[45] Date of Patent: Feb. 10, 1987

[54] CIRCULATION-ACTIVE TETRAHYDROTHIENOPYRIDINES

[75] Inventors: Siegfried Goldmann, Wuppertal; Matthias Schramm, Cologne; Günter Thomas; Rainer Gross, both of Wuppertal, all of Fed. Rep. of Germany

[73] Assignee: Bayer Aktiengesellschaft, Leverkusen, Fed. Rep. of Germany

[21] Appl. No.: 716,876

[22] Filed: Mar. 28, 1985

[30] Foreign Application Priority Data

Apr. 6, 1984 [DE] Fed. Rep. of Germany ....... 3412947

[51] Int. Cl.$^4$ .................. A61K 31/38; C07D 513/04; C07D 417/02
[52] U.S. Cl. ........................... 514/301; 546/114; 544/126; 544/361; 544/354; 544/356; 544/253; 544/238; 544/298; 544/300; 544/322; 544/324; 544/333; 544/284
[58] Field of Search ............ 546/114; 544/126; 514/301

[56] References Cited

U.S. PATENT DOCUMENTS 3,935,220  1/1976  Meyer et al. ..................... 546/114
3,948,923  4/1976  Meyer et al. ..................... 546/114
4,338,322  7/1982  Sato ................................. 546/114

OTHER PUBLICATIONS

Goodman and Gilman, The Pharmacological Basis of Therapeutics, 6th ed., p. 28.

Primary Examiner—Henry R. Jiles
Assistant Examiner—J. Richter
Attorney, Agent, or Firm—Sprung Horn Kramer & Woods

[57] ABSTRACT

Tetrahydrothienopyridines of the formula

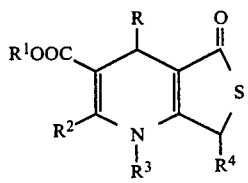

in which
R is optionally substituted aryl or heterocyclyl,
$R^1$ is an organic radical, and
$R^2$, $R^3$ and $R^4$ each independently is hydrogen or an organic radical, or pharmaceutically acceptable salts thereof, which are coronary active, hypotensive, anti-diabetic and salt balance restoring.

12 Claims, No Drawings

CIRCULATION-ACTIVE TETRAHYDROTHIENOPYRIDINES

The present invention relates to new tetrahydrothienopyridines, a process for their preparation and their use as medicaments, in particular as medicaments which influence the circulation.

The new compounds are characterised by the following general formula (I)

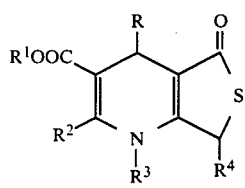

in which
- R represents a phenyl, naphthyl, thienyl, furyl, pyrryl, pyrazolyl, imidazolyl, oxazolyl, isoxazolyl, thiazolyl, pyridyl, pyridazinyl, pyrimidyl, pyrazinyl, quinolyl, isoquinolyl, indolyl, benzimidazolyl, quinazolyl, quinoxalyl, thionaphthenyl, isothionaphthenyl, chromonyl, thiochromonyl, chromenyl, thiochromenyl, benzoxadiazolyl or benzothiadiazolyl radical, it being possible for the radicals mentioned optionally to contain 1 to 3 identical or different substituents from the group comprising alkyl (1 to 20 carbon atoms), alkenyl (1 to 20 carbon atoms), alkinyl (1 to 20 C atoms), alkoxy (1 to 20 C atoms), fluorine, chlorine, bromine, iodine, trifluoromethyl, monofluoroalkoxy (1 to 10 C atoms), polyfluoroalkoxy (1 to 10 C atoms), hydroxyl, amino, monoalkylamino (1 to 10 C atoms), dialkylamino (1 to 10 C atoms), nitro, cyano, azido, carboxyl, carbalkoxy, carboxamido, sulphonamido, $SO_m$-alkyl (m=0 to 2, 1 to 20 C atoms), phenyl, benzyl, benzyloxy and benzylthio, it being possible for the last four substituents mentioned optionally to contain 1 to 3 radicals from the group comprising alkyl (1 to 5 C atoms), alkoxy (1 to 5 C atoms), alkylthio (1 to 5 C atoms), fluorine, chlorine, bromine, iodine, cyano, nitro, azido, hydroxyl, trifluoromethyl, amino, alkylamino (1 to 6 C atoms) or dialkylamino (in each case 1 to 6 C atoms),
- $R^1$ represents a straight-chain, branched or cyclic saturated or unsaturated hydrocarbon radical (1 to 20 C atoms), which can optionally be interrupted in the chain by 1 or 2 oxygen or sulphur atoms and which can optionally be substituted by one or more fluorine atoms, $NO_2$, trialkylsilyl (3 to 12 C atoms), —OH, —Cl, Br, I, —CN, amino, alkylamino (1 to 10 C atoms), dialkylamino (in each case 1 to 10 C atoms), benzylalkylamino (alkyl radical with 1 to 8 C atoms), phenyl, naphthyl or pyridyl,
- $R^2$ represents hydrogen, —NH$_2$, —CHO, —CN, —CH$_2$OH or a straight-chain or branched, saturated or unsaturated hydrocarbon radical (up to 8 C atoms),
- $R^3$ represents hydrogen or a straight-chain or branched alkyl radical (1 to 10 C atoms), which is optionally interrupted in the alkyl chain by one or two oxygen atoms and can optionally be substituted by fluorine, chlorine, bromine, iodine, —CN, —NH$_2$, —OH or morpholino, and
- $R^4$ represents hydrogen or a straight-chain or branched alkyl radical (1 to 10 C atoms)

in the form of isomers, isomer mixtures, racemates, optical antipodes and their pharmaceutically acceptable salts.

Examples of salts which may be mentioned are the hydrochlorides, hydrogen sulphates, sulphates, hydrogen phosphates, acetates, maleates, benzoates, citrates, tartrates and lactates.

Compounds of the general formula (I) which are of particular interest are those in which
- R represents a phenyl, naphthyl, thienyl, pyrryl, imidazolyl, oxazolyl, isoxazolyl, thiazolyl, pyridyl, pyridazinyl, pyrimidyl, quinolyl, isoquinolyl, indolyl, benzimidazolyl, quinazolyl, thionaphthenyl, chromonyl, thiochromonyl, chromenyl, thiochromenyl, benzoxadiazolyl or benzothiadiazolyl radical, it being possible for the radicals mentioned optionally to contain 1 to 3 identical or different substituents from the group comprising alkyl (1 to 15 carbon atoms), alkenyl (1 to 15 carbon atoms), alkinyl (1 to 15 C atoms), alkoxy (1 to 15 C atoms), fluorine, chlorine, bromine, iodine, trifluoromethyl, monofluoroalkoxy (1 to 5 C atoms), polyfluoroalkoxy (1 to 5 C atoms), hydroxy-amino, monoalkylamino (1 to 5 C atoms), dialkylamino (1 to 5 C atoms), nitro, cyano, azido, carboxyl, carboxamido, sulphonamido, $SO_m$-alkyl (m=0 to 2, 1 to 10 C atoms), phenyl-, benzyl-, benzyloxy- and benzylthio-, it being possible for the last four substituents mentioned optionally to contain 1 to 3 radicals from the group comprising alkyl (1 to 4 C atoms), alkoxy (1 to 4 C atoms), alkylthio (1 to 4 C atoms), fluorine, chlorine, cyano, nitro, hydroxyl, trifluoromethyl fluoromethyl, amino, alkylamino (1 to 4 C atoms) or dialkylamino (1 to 4 C atoms),
- $R^1$ represents a straight-chain, branched or cyclic saturated or unsaturated hydrocarbon radical (1 to 15 C atoms), which can optionally be interrupted in the chain by 1 or 2 oxygen or sulphur atoms and can optionally be substituted by one or more fluorine atoms, $NO_2$, trialkylsilyl (3 to 9 C atoms), —OH, —Cl, —CN, amino, alkylamino (1 to 5 C atoms) or dialkylamino (in each case 1 to 5 C atoms),
- $R^2$ represents hydrogen, —CHO, —CN or a straight-chain or branched, saturated or unsaturated hydrocarbon radical (1 to 6 C atoms),
- $R^3$ represents hydrogen or a straight-chain or branched alkyl radical (1 to 6 C atoms), which is optionally interrupted in the alkyl chain by one or two oxygen atoms and can optionally be substituted by fluorine, chlorine, —CN, —OH or morpholino, and
- $R^4$ represents hydrogen or a straight-chain or branched alkyl radical (1 to 6 C atoms).

Compounds of the general formula (I) which may be mentioned as preferred are those in which
- R represents a phenyl, naphthyl, thienyl, oxazolyl, isoxazolyl, thiazolyl, pyridyl, pyrimidyl, quinolyl, isoquinolyl, indolyl, benzimidazolyl, quinazolyl, thionaphthenyl, chromonyl, thiochromonyl, chromenyl, thiochromenyl, benzoxadiazolyl or benzothiadiazolyl radical, it being possible for the radicals mentioned optionally to contain 1 or 2 identical or different substituents from the group comprising alkyl- (1 to 10 carbon atoms), alkenyl- (1 to 10 carbon atoms), alkoxy (1 to 10 C atoms), fluorine, chlorine, bromine, trifluoromethyl, monofluoroalkoxy- (1 to 5 C atoms), polyfluoroalkoxy-(1 to 5 C atoms), hydroxyl-, monoalkylamino-(1 to 5 C atoms), dialkylamino- (1 to 5 C atoms), nitro, cyano, azido, $SO_m$-alkyl (m=0 to 2, 1 to 5 C atoms), phenyl-, benzyl-, benzyloxy- and benzylthio, it being possible for the last four substituents mentioned optionally to contain 1 to 3 radicals from the group comprising alkyl (1 to 3 C atoms), alkoxy (1 to 3 C atoms), alkylthio (1 to 3 C atoms), fluorine, chlorine, cyano, nitro and trifluoromethyl-, $R^1$ represents a straight-chain, branched or cyclic, saturated or unsaturated hydrocarbon radical (1 to 10 C atoms), which can optionally be interrupted in the chain by 1 or 2 oxygen or sulphur atoms and can optionally be substituted by one or more fluorine atoms, $NO_2$, trialkylsilyl (3 to 6 C atoms), —OH, —Cl, —CN, amino, alkylamino (1 to 3 C atoms) or dialkylamino (in each case 1 to 3 C atoms), $R^2$ represents hydrogen or a straight-chain or branched, saturated or unsaturated hydrocarbon radical (1 to 4 C atoms), $R^3$ represents hydrogen or a straight-chain or branched alkyl radical (1 to 4 C atoms), which is optionally interrupted in the alkyl chain by 1 or 2 oxygen atoms and can optionally be substituted by fluorine, chlorine, —OH or morpholino, and $R^4$ represents hydrogen or a straight-chain alkyl radical (1 to 4 C atoms).

The compounds of the general formula (I) according to the invention can be prepared by a process in which benzylidene compounds of the general formula (II)

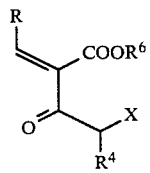
(II)

in which
R and $R^4$ have the abovementioned meaning,
X represents halogen and
$R^6$ represents an alkyl radical with up to 6 carbon atoms,
are reacted with thiolates of the general formula (III)

 (III)

in which
Me denotes an alkali metal and
$R^5$ represents a thiol-protective group,
in the presence of inert organic solvents at temperatures of $-60°$ to $+80°$ C., alkali metal halide (MeX) being split off, to give compounds of the general formula (IV)

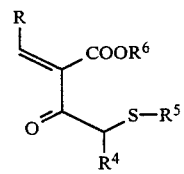
(IV)

in which
R, $R^4$, $R^5$ and $R^6$ have the abovementioned meaning,
and the compound of the formula (IV) is then reacted with aminocrotonic acid esters of the general formula (V)

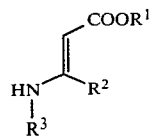
(V)

in which
$R^1$, $R^2$ and $R^3$ have the abovementioned meaning, in the presence of inert organic solvents to give the dihydropyridine of the general formula (VI)

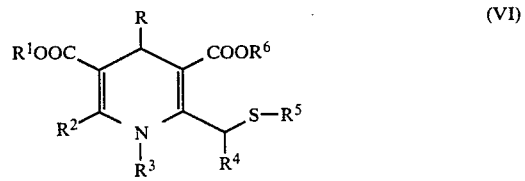
(VI)

in which
R, $R^1$, $R^2$, $R^3$, $R^4$, $R^5$ and $R^6$ have the abovementioned meaning,
and this dihydropyridine of the formula (VI) is then lactonized, the thiol-protective group ($R^5$) being split off, to give compounds of the general formula (I).

The reaction steps in the process according to the invention can be carried out either as a one-pot reaction, without the intermediates (IV) and (VI) formed being isolated, or in separate reaction stages, the intermediates (IV) and (VI) being isolated.

Acyl groups with up to 8 carbon atoms or tertiary alkyl groups, in particular tertiary butyl, may be mentioned as preferred thiol-protective groups ($R^5$).

Lithium, sodium and potassium may be mentioned as the preferred alkali metal (Me).

Lower alcohols with up to 6 carbon atoms may be mentioned as preferred solvents for the reaction of (II) to give (IV).

Chlorine and bromine may be mentioned as the preferred halogen (X).

The thiol-protective group is preferably split off from compounds of the general formula (VI) with suitable reagents for splitting off this group, such as, for example, organic and inorganic acids.

The thiol group (S-$R^5$) is preferably introduced at temperatures between $-20°$ and $+60°$ C., in particular between $0°$ and $30°$ C.

The benzylidene compounds of the general formula (II) are known, or they can be prepared by known methods (compare: Surrey et al. JACS 66, 1933 (1944)).

The sulphur compounds of the general formula (III) used for the preparation are known, or they can be prepared by known methods (compare C. Ulrich, Ann. 109 (1958), 272).

The aminocrotonic acid esters of the general formula (V) used in the preparation are likewise known, or they can be prepared by known methods (compare: A. C. Cope, J. Am. Chem. Soc. 67, 1017 (1945)).

The following compounds according to the invention may be mentioned as examples, in addition to the compounds in the preparation examples: (1) ethyl 4-(2-benzylthiophenyl)-2-methyl-5-oxo-1,4,5,7-tetrahydro-thieno[3,4-b]pyridine-3-carboxylate, (2) methyl 4-(2-benzyloxyphenyl)-2-methyl-5-oxo-1,4,5,7-tetrahydro-thieno[3,4-b]pyridine-3-carboxylate, (3) butyl 4-(3-chlorophenyl)-2-methyl-5-oxo-1,4,5,7-tetrahydro-thieno[3,4-b]pyridine-3-carboxylate, (4) ethyl 2-cyano-4-(2-methylphenyl)-5-oxo-1,4,5,7-tetrahydrothieno[3,4-b]pyridine-3-carboxylate, (5) ethyl 2-methyl-5-oxo-4-(4-oxo-2-phenyl-4H-chromen-8-yl)-1,4,5,7-tetrahydro-thieno[3,4-b]pyridine-3-carboxylate, (6) ethyl 2-methyl-4-(2-[4-methylbenzyl]thiophenyl)-5-oxo-1,4,5,7-tetrahy-drothieno[3,4-b]pyridine-3-carboxylate and (7) (N-ben-zyl-N-methyl)-aminoethyl 2-methyl-5-oxo-4-(2-tri-fluoromethylphenyl)-1,4,5,7-tetrahydrothieno[3,4-b]pyridine-3-carboxylate.

The compounds according to the invention exhibit a useful pharmacological action spectrum which could not be predicted. They can be used as cardiotonic agents for improving the contractility of the heart. Moreover, since they increase the flow of Ca++ into the cells, they can be used as antihypotensives, for re-duction of blood sugar, for detumescence of mucous membranes and for influencing the salt and/or fluid balance.

The compounds according to the invention can be converted in a known manner into the customary for-mulations, such as tablets, capsules, dragees, pills, gran-ules, aerosols, syrups, emulsions, suspensions and solu-tions, using inert, non-toxic, pharmaceutically suitable excipients or solvents. The therapeutically active com-pound should in each case be present in a concentration of about 0.5 to 90% by weight of the total mixture, that is to say in amounts which suffice to achieve the indi-cated dosage range.

The formulations are prepared, for example, by ex-tending the active compounds with solvents and/or excipients, using emulsifying agents and/or dispersing agents if appropriate, and, for example in the case of water being used as the diluent, organic solvents can be employed as auxiliary solvents, if appropriate.

Examples of auxiliaries which may be mentioned are: water, non-toxic organic solvents, such as paraffins (for example petroleum fractions), vegetable oils (for exam-ple groundnut/sesame oil), alcohols (for example ethyl alcohol and glycerol) and glycols (for example propy-lene glycol and polyethylene glycol), solid excipients, such as, for example, natural rock powders (for example kaolins, aluminas, talc and chalk), synthetic rock pow-ders (for example highly disperse silica and silicates) and sugars (for example sucrose, lactose and glucose), emulsifying agents (for example polyoxyethylene fatty acid ester, polyoxyethylene fatty alcohol ethers, alkyl-sulphonates and arylsulphonates), dispersing agents (for example lignin, sulphite waste liquors, methylcellulose, starch and polyvinylpyrrolidone) and lubricants (for example magnesium stearate, talc, stearic acid and so-dium lauryl-sulphate).

Administration is effected in the customary manner, preferably orally or parenterally, in particular perlingu-ally or intravenously. In the case of oral use, tablets can of course also contain, in addition to the excipients mentioned, additives, such as sodium citrate, calcium carbonate and dicalcium phosphate, together with vari-ous further substances, such as starch, preferably potato starch, gelatine and the like. Furthermore, lubricants, such as magnesium stearate, sodium laurylsulphate and talc, can be used conjointly for tablet-making. In the case of aqueous suspensions and/or elixirs intended for oral use, the active compounds can be mixed with vari-ous flavor-improving agents or dyestuffs, in addition to the abovementioned auxiliaries.

In the case of parenteral administration, solutions of the active compounds can be employed, using suitable liquid excipients.

In general, it has proved advantageous, in the case of intravenous administration, to administer amounts of about 0.0001 to 1 mg/kg, preferably about 0.001 to 0.5 mg/kg of body weight daily to achieve effective results whilst in the case of oral administration the dosage is about 0.01 to 20 mg/kg, preferably 0.1 to 10 mg/kg of body weight daily.

Nevertheless, it may at times be necessary to deviate from the amounts mentioned, and in particular to do so as a function of the body weight of the experimental animal or the nature of the administration route, but also because of the species of animal and its individual be-havior towards the medicament or the nature of its formulation and the time or interval at which it is ad-ministered. Thus, in some cases it may suffice to manage with less than the abovementioned minimum amount, whilst in other cases the upper limit mentioned must be exceeded. Where major amounts are administered, it can be advisable to divide these into several individual administrations over the course of the day. The same dosage range is envisaged for administration in human medicine. Here, again, the general sense of the above comments applies.

EMBODIMENT EXAMPLES

Example 1

Ethyl 2-methyl-5-oxo-4-(2-trifluoromethylphenyl)-1,4,5,7-tet-rahydrothieno[3,4-b]pyridine-3-carboxylate

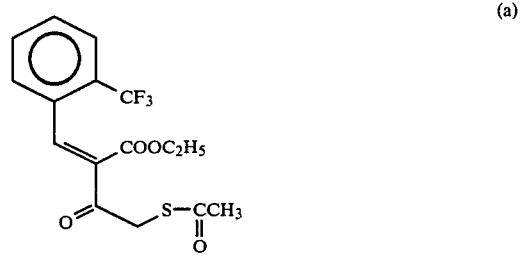

(a)

50 mmol of ethyl 4-chloro-2-(2-trifluoromethylben-zylidene)-3-ketobutyrate (E/Z mixture) are dissolved in 100 ml of ethanol, and 50 mmol of potassium thioacetate are added at 0° C., the mixture is stirred at room temper-ature for 2 hours and concentrated, the residue is taken up in CH$_2$Cl$_2$ and the mixture is washed with water and dried. Ethyl 4-acetylthio-2-(2-trifluoromethylben-zylidene)-3-ketobutyrate (E/Z mixture) remains as an oil.

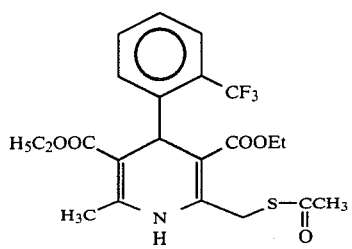

The oil obtained above is boiled under reflux with 50 mmol of ethyl 3-aminocrotonate in 50 ml of ethanol overnight, the mixture is concentrated and the residue is chromatographed on silica gel with toluene/ethyl acetate (8:2).

Diethyl 2-acetylthiomethyl-6-methyl-4-(2-trifluoromethylphenyl)-1,4-dihydropyridine-3,5-dicarboxylate remains.

MS (471, M⊕), 326 (100%), 284 (40%) and 238 (20%)

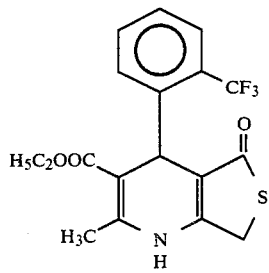

10 mmol of diethyl 2-acetylthiomethyl-6-methyl-4-(2-trifluoromethylphenyl)-1,4-dihydropyridine-3,5-dicarboxylate, dissolved in 40 ml of ethanol, are boiled with 6 ml of saturated ethanolic HCl for 2 hours and the product is precipitated with water and then recrystallized from ethanol.

Melting point: 213°–216° C.

Example 2 (Preparation analogous to Example 1)

Ethyl 2-methyl-5-oxo-4-(4-oxo-2-phenyl-4H-thiochromen-8-yl)-1,4,5,7-tetrahydrothieno[3,4-b]pyridine-3-carboxylate

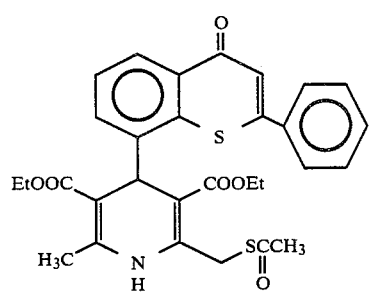

Preparation analogous to Example 1, melting point: 120° C.

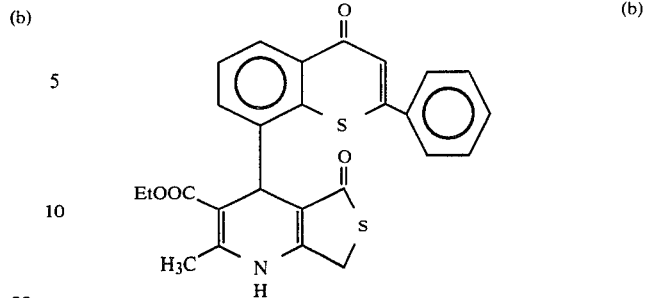

Preparation analogous to Example 1, melting point: >270° C.

$^1$H-NMR (DMSO): 0.8 (3H,t), 2.4 (s, 3H), 3.9 (q, 2H), 4.1 and 4.3 (2d, 1H each), 5.4 (s, 1H), 7.25 (s, 1H), 7.6 (m, 5H), 7.9 (m, 2H), 8.3 (dd, 1H) and 10.2 (s, NH).

Example 3

Butyl 2-methyl-5-oxo-4-(4-oxo-2-phenyl-4H-thiochromen-8-yl)-1,4,5,7-tetrahydrothieno[3,4-b]pyridine-3-carboxylate Preparation analogous to Example 2, but without isolation of intermediates.

Melting point: 210° to 220° C.

Example 4

Methyl 2-methyl-5-oxo-4-(2-methylphenyl)-1,4,5,7-tetrahydrothieno[3,4-b]pyridine-3-carboxylate Preparation analogous to Example 3, melting point: 240° to 43° C.

Example 5

Butyl 2-methyl-5-oxo-4-(2-methylphenyl)-1,4,5,7-tetrahydrothieno[3,4-b]pyridine-3-carboxylate Preparation analogous to Example 3, melting point: 160° to 163° C.

Example 6

Ethyl 4-(2-chlorophenyl)-2-methyl-5-oxo-1,4,5,7-tetrahydrothieno[3,4-b]pyridine-3-carboxylate Preparation analogous to Example 3, melting point: 234° to 237° C.

Example 7

Methyl 2-methyl-5-oxo-4-(4-oxo-2-phenyl-4H-thiochromen-8-yl)-1,4,5,7-tetrahydrothieno[3,4-b]pyridine-3-carboxylate Preparation analogous to Example 3, melting point: >270° C. MS: 461 (M+, 30%), 402 (30%), 238 (80%), 224 (50%) and 44 (100%).

It will be understood that the specification and examples are illustrative but not limitative of the present invention and that other embodiments within the spirit and scope of the invention will suggest themselves to those skilled in the art.

Pharmacological activity

| Example 1c | |
|---|---|
| Isolated Perfused | |
| dp/dt-increase | Auricle (IVM) |
| +20% | $10^{-7}$ g/ml |
| +30% | $10^{-6}$ g/ml |
| +40% | $10^{-5}$ g/ml |

What is claimed is:

1. A tetrahydrothienopyridine of the formula

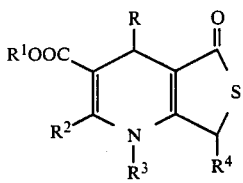

in which

R represents a phenyl, naphthyl, thienyl, thionaphthenyl, isothionaphthenyl, thiochromonyl or thiochromenyl radical, it being possible for the radicals mentioned optionally to contain 1 to 3 identical or different substituents from the group comprising alkyl (1 to 20 carbon atoms), alkenyl (1 to 20 carbon atoms), alkinyl (1 to 20 carbon atoms), alkoxy (1 to 20 carbon atoms), fluorine, chlorine, bromine, iodine, trifluoromethyl, monofluoroalkoxy (1 to 10 C atoms), polyfluoroalkoxy (1 to 10 C atoms), hydroxyl, amino, monoalkylamino (1 to 10 C atoms), dialkylamino (1 to 10 C atoms), nitro, cyano, azido, carboxyl, carbalkoxy, carboxamido, sulphonamido, $SO_m$-alkyl (m=0 to 2, 1 to 20 C atoms), phenyl-, benzyl-, benzyloxy and benzylthio, it being possible for the last four substituents mentioned optionally to contain 1 to 3 radicals from the group comprising alkyl (1 to 5 C atoms), alkoxy (1 to 5 C atoms), alkylthio (1 to 5 C atoms), fluorine, chlorine, bromine, iodine, cyano, nitro, azido, hydroxyl, trifluoromethyl, amino, alkylamino (1 to 6 C atoms) or dialkylamino (in each case 1 to 6 C atoms), $R^1$ represents a straight-chain, branched or cyclic saturated or unsaturated hydrocarbon radical (1 to 20 C atoms), which can optionally be interrupted in the chain by 1 or 2 oxygen or sulphur atoms and which can optionally be substituted by one or more fluorine atoms, $NO_2$, trialkylsilyl (3 to 12 C atoms), —OH, —Cl, Br, I, —CN, amino, alkylamino (1 to 10 C atoms), dialkylamino (in each case 1 to 10 C atoms), benzylalkylamino (alkyl radical with 1 to 8 C atoms), phenyl, naphthyl or pyridyl, $R^2$ represents hydrogen, —$NH_2$, —CHO, —CN, —$CH_2OH$ or a straight-chain or branched, saturated or unsaturated hydrocarbon radical (up to 8 C atoms), $R^3$ represents hydrogen or a straight-chain or branched alkyl radical (1 to 10 C atoms) which is optionally interrupted in the alkyl chain by one or two oxygen atoms and can optionally be substituted by fluorine, chlorine, bromine, iodine, —CN, —$NH_2$, —OH or morpholino, and $R^4$ represents hydrogen or a straight-chain or branched alkyl radical (1 to 10 C atoms), or a pharmaceutically acceptable salt thereof.

2. A compound or salt according to claim 1, in which R represents a phenyl, naphthyl, thienyl, thionaphthenyl, thiochromonyl or thiochromenyl radical, it being possible for the radicals mentioned optionally to contain 1 to 3 identical or different substituents from the group comprising alkyl (1 to 15 carbon atoms), alkenyl (1 to 15 carbon atoms), alkinyl (1 to 15 C atoms), alkoxy (1 to 15 C atoms), fluorine, chlorine, bromine, iodine, trifluoromethyl, monofluoroalkoxy (1 to 5 C atoms), polyfluoroalkoxy (1 to 5 C atoms), hydroxy-amino, monoalkylamino-(1 to 5 C atoms), dialkylamino (1 to 5 C atoms), nitro, cyano, azido, carboxyl, carboxamido, sulphonamido, $SO_m$-alkyl (m=0 to 2, 1 to 10 C atoms), phenyl, benzyl, benzyloxy and benzylthio, it being possible for the last four substituents mentioned optionally to contain 1 to 3 radicals from the group comprising alkyl (1 to 4 C atoms), alkoxy (1 to 4 C atoms), alkylthio (1 to 4 C atoms), fluorine, chlorine, cyano, nitro, hydroxyl, trifluoromethyl, amino, alkylamino (1 to 4 C atoms) or dialkylamino (1 to 4 C atoms), $R^1$ represents a straight-chain, branched or cyclic saturated or unsaturated hydrocarbon radical (1 to 15 C atoms), which can optionally be interrupted in the chain by 1 or 2 oxygen or sulphur atoms and can optionally be substituted by one or more fluorine atoms, $NO_2$, trialkylsilyl (3 to 9 C atoms), —OH, —Cl, —CN, amino, alkylamino (1 to 5 C atoms) or dialkylamino (in each case 1 to 5 C atoms), $R^2$ represents hydrogen, —CHO, —CN or a straight-chain or branched, saturated or unsaturated hydrocarbon radical (1 to 6 C atoms), $R^3$ represents hydrogen or a straight-chain or branched alkyl radical (1 to 6 C atoms), which is optionally interrupted in the alkyl chain by one or two oxygen atoms and can optionally be substituted by fluorine, chlorine, —CN, —OH or morpholino, and $R^4$ represents hydrogen or a straight-chain or branched alkyl radical (1 to 6 C atoms).

3. A compound or salt according to claim 1, in which R represents a phenyl, naphthyl, thienyl, thionaphthenyl, thiochromonyl or thiochromenyl radical, it being possible for the radicals mentioned optionally to contain 1 or 2 identical or different substituents from the group comprising alkyl (1 to 10 carbon atoms), alkenyl (1 to 10 carbon atoms), alkoxy (1 to 10 C atoms), fluorine, chlorine, bromine, trifluoromethyl, monofluoroalkoxy (1 to 5 C atoms), polyfluoroalkoxy (1 to 5 C atoms), hydroxyl, monoalkylamino (1 to 5 C atoms), dialkylamino (1 to 5 C atoms), nitro, cyano, azido, $SO_m$-alkyl (m=0 to 2, 1 to 5 C atoms), phenyl, benzyl, benzyloxy and benzylthio, it being possible for the last four substituents mentioned optionally to contain 1 to 3 radicals from the group comprising alkyl (1 to 3 C atoms), alkoxy (1 to 3 C atoms), alkylthio (1 to 3 C atoms), fluorine, chlorine, cyano, nitro and trifluoromethyl, $R^1$ represents a straight-chain, branched or cyclic, saturated or unsaturated hydrocarbon radical (1 to 10 C atoms), which can optionally be interrupted in the chain by 1 or 2 oxygen or sulphur atoms and can optionally be substituted by one or more fluorine atoms, $NO_2$, trialkylsilyl (3 to 6 C atoms), —OH, —Cl, —CN, amino, alkylamino (1 to 3 C atoms) or dialkylamino (in each case 1 to 3 C atoms), R² represents hydrogen or a straight-chain or branched, saturated or unsaturated hydrocarbon radical (1 to 4 C atoms), R³ represents hydrogen or a straight-chain or branched alkyl radical (1 to 4 C atoms), which is optionally interrupted in the alkyl chain by 1 or 2 oxygen atoms and can optionally be substituted by fluorine, chlorine, —OH or morpholino, and R⁴ represents hydrogen or a straight-chain alkyl radical (1 to 4 C atoms).

4. A tetrahydrothienopyridine according to claim 1, wherein such tetrahydrothienopyridine is ethyl 2-methyl-5-oxo-4-(2-trifluoromethylphenyl)-1,4,5,7-tetrahydrothieno[3,4-b]pyridine-3-carboxylate of the formula

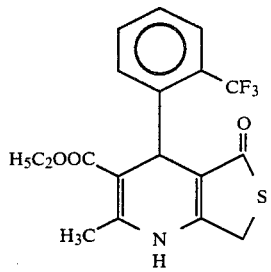

or a pharmaceutically acceptable salt thereof.

5. A tetrahydrothienopyridine according to claim 1, wherein such tetrahydrothienopyridine is ethyl 2-methyl-5-oxo-4-(4-oxo-2-phenyl-4H-thiochromen-8-yl)-1,4,5,7-tetrahydrothieno[3,4-b]pyridine-3-carboxylate of the formula

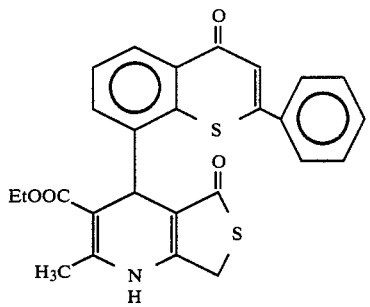

or a pharmaceutically acceptable salt thereof.

6. A tetrahydrothienopyridine according to claim 1, wherein such tetrahydrothienopyridine is methyl 2-methyl-5-oxo-4-(2-methylphenyl)-1,4,5,7-tetrahydrothieno[3,4-b]pyridine-3-carboxylate of the formula

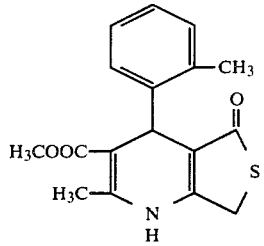

or a pharmaceutically acceptable salt thereof.

7. A tetrahydrothienopyridine according to claim 1, wherein such tetrahydrothienopyridine is methyl 2-methyl-5-oxo-4-(4-oxo-2-phenyl-4H-thiochromen-8-yl)-1,4,5,7-tetrahydrothieno[3,4-b]pyridine-3-carboxylate of the formula

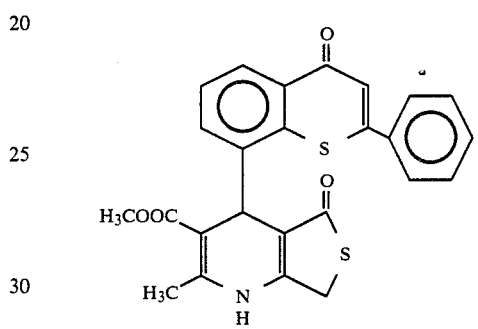

or a pharmaceutically acceptable salt thereof.

8. A cardiotonic agent for combating circulation disorders, hypotension, diabetes and salt imbalance in a patient comprising an amount effective therefor of a tetrahydrothienopyridine or salt according to claim 1 in admixture with a diluent.

9. A unit dose of a cardiotonic agent according to claim 1 in the form of a tablet, capsule of ampule.

10. A method of combating hypotension, diabetes or a salt imbalance in a patient in need thereof which comprises administering an amount effective therefor of a tetrahydrothienopyridine or salt according to claim 1.

11. The method according to claim 10, wherein said tetrahydrothienopyridine is selected from the group consisting of ethyl 2-methyl-5-oxo-4-(2-trifluoromethylphenyl)-1,4,5,7-tetrahydrothieno[3,4-b]pyridine-3-carboxylate, ethyl 2-methyl-5-oxo-4-(4-oxo-2-phenyl-4H-thiochromen-8-yl)-1,4,5,7-tetrahydrothieno[3,4-b]pyridine-3-carboxylate, methyl 2-methyl-5-oxo-4-(2-methylphenyl)-1,4,5,7-tetrahydrothieno[3,4-b]pyridine-3-carboxylate or methyl 2-methyl-5-oxo-4-(4-oxo-2-phenyl-4H-thiochromen-8-yl)-1,4,5,7-tetrahydrothieno[3,4-b]pyridine-3-carboxylate, or pharmaceutically acceptable salt thereof.

12. A cardiotonic agent according to claim 8, wherein the tetrahydrothienopyridine is present in a concentration of 0.5 to 90% by weight of the total.

* * * * *